United States Patent [19]

Mitchnick et al.

[11] Patent Number: 5,441,726
[45] Date of Patent: Aug. 15, 1995

[54] TOPICAL ULTRA-VIOLET RADIATION PROTECTANTS

[75] Inventors: Mark Mitchnick, Wainscott, N.Y.; Mamoun Muhammed, Djursholm, Sweden

[73] Assignee: SunSmart, Inc., Wainscott, N.Y.

[21] Appl. No.: 54,038

[22] Filed: Apr. 28, 1993

[51] Int. Cl.$^6$ ................................................ A61K 7/42
[52] U.S. Cl. .................................. 424/59; 106/14.34; 106/18.27; 106/425; 106/14.39; 428/540; 524/432; 423/622
[58] Field of Search ................... 424/59, 60; 423/621, 423/622, 610

[56] References Cited

U.S. PATENT DOCUMENTS

| | | | |
|---|---|---|---|
| 2,898,191 | 8/1959 | Conn et al. | 423/622 |
| 2,900,244 | 8/1959 | Bradstreet et al. | 75/359 |
| 3,052,539 | 9/1962 | Greig et al. | 96/1 |
| 3,397,257 | 8/1968 | Brambilla et al. | 252/635 |
| 3,441,370 | 4/1969 | Gutmann et al. | 23/2 |
| 3,639,162 | 2/1972 | Bixler | 117/215 |
| 3,754,909 | 8/1973 | Feltzin et al. | 96/1.5 |
| 3,972,715 | 8/1976 | Okumura | 96/1 R |
| 4,048,372 | 9/1977 | Ando et al. | 428/412 |
| 4,160,046 | 7/1979 | Okumura | 427/57 |
| 4,239,632 | 12/1980 | Baile | 252/12 |
| 4,261,965 | 4/1981 | Fukuda et al. | 423/544 |
| 4,262,318 | 4/1981 | Shirakawa et al. | 361/127 |
| 4,382,024 | 5/1983 | Seaman et al. | 252/511 |
| 4,418,117 | 11/1983 | Shaw | 428/327 |
| 4,420,534 | 12/1983 | Matsui et al. | 428/372 |
| 4,457,973 | 7/1984 | Matsui et al. | 428/372 |
| 4,495,482 | 1/1985 | Philipp | 338/21 |
| 4,543,341 | 9/1985 | Barringer et al. | 501/1 |
| 4,571,361 | 2/1986 | Kawaguchi et al. | 428/328 |
| 4,604,303 | 8/1986 | Kakakura et al. | 427/229 |
| 4,606,869 | 8/1986 | Showak | 264/12 |
| 4,634,630 | 1/1987 | Kamijyo | 428/399 |
| 4,642,202 | 2/1987 | Railsback | 252/511 |
| 4,655,811 | 4/1987 | Bitter | 65/60.51 |
| 4,689,475 | 8/1987 | Kleiner et al. | 219/553 |
| 4,721,610 | 1/1988 | Yoshida et al. | 423/636 |
| 4,722,763 | 2/1988 | Pa et al. | 156/616.1 |
| 4,738,720 | 4/1988 | Eckler et al. | 106/14.05 |
| 4,758,281 | 7/1988 | Eckler et al. | 106/467 A |
| 4,808,398 | 2/1989 | Heistand, II | 423/622 |
| 4,842,832 | 6/1989 | Inoue et al. | 423/610 |
| 4,869,954 | 9/1989 | Squitieri | 428/283 |
| 4,876,777 | 10/1989 | Chow | 29/132 |
| 4,880,703 | 11/1989 | Sakamoto et al. | 428/378 |
| 4,910,389 | 3/1990 | Sherman et al. | 219/548 |
| 4,923,518 | 5/1990 | Brand et al. | 106/429 |
| 4,971,727 | 11/1990 | Takahashi et al. | 252/511 |
| 5,008,646 | 4/1991 | Hennings et al. | 338/20 |
| 5,026,594 | 6/1991 | Akao | 428/220 |
| 5,032,390 | 7/1991 | Iwaya et al. | 424/59 |
| 5,053,444 | 10/1991 | Trotoir | 523/351 |
| 5,066,475 | 11/1991 | Yoshinaka et al. | 423/622 |
| 5,071,692 | 12/1991 | Jourdaine | 428/192 |
| 5,091,765 | 2/1992 | Yoshinaka et al. | 357/30 |
| 5,093,099 | 3/1992 | Haishi et al. | 423/622 |
| 5,102,650 | 4/1992 | Hayashi et al. | 423/622 |
| 5,104,731 | 4/1992 | Gager | 428/323 |
| 5,106,538 | 4/1992 | Barma et al. | 252/511 |
| 5,132,104 | 7/1992 | Yamamoto et al. | 423/419 P |
| 5,162,775 | 11/1992 | Kuramochi et al. | 338/114 |
| 5,173,333 | 12/1992 | Tranbarger et al. | 427/236 |
| 5,173,765 | 12/1992 | Nakayoshi et al. | 257/783 |

FOREIGN PATENT DOCUMENTS

| | | | |
|---|---|---|---|
| 0317272 | 5/1989 | European Pat. Off. | |
| 0433086A1 | 6/1991 | European Pat. Off. | 424/59 |
| 62-260716 | 11/1987 | Japan | |
| 2311314 | 12/1990 | Japan | 423/622 |

Primary Examiner—Jane Fan
Attorney, Agent, or Firm—Weingarten, Schurgin, Gagnebin & Hayes

[57] ABSTRACT

Disclosed are compositions for application to a surface to protect the surface from ultra-violet radiation, which include zinc oxide particles having a substantially rod shape.

13 Claims, 5 Drawing Sheets

TOPICAL ULTRA-VIOLET RADIATION PROTECTANTS

The invention relates to topical applications which provide protection from ultra-violet radiation.

BACKGROUND OF THE INVENTION

Ultraviolet (UV) radiation having a wavelength falling within the range of 290-400 nanometers (nm) has been associated with damage to human skin. UV-B radiation is produced between 290-320 nm and UV-A radiation between 320-400 nm. UV radiation damage to human skin may result in damage to the dermal infrastructure which, in its most extreme form may result in malignancies. UV radiation falling within the range of 290-320 nm may cause erythema and edema associated with sunburn.

Sunscreens which have been used in an attempt to block out harmful UV rays include organic sunscreens such as para-aminobenzoic acid (PABA). However, organic sunscreens do not block both UV-B and UV-A rays, and may have side-effects such as irritation and toxicity. Inorganic sunscreens offer broader protection in that they block radiation generally within the range of 290-366 nm. Inorganic sunscreens most often are made of particles of titanium dioxide or zinc oxide which lie on the skin surface. Since these particles are not absorbed by the skin, they usually do not produce skin irritation or toxic side effects.

UV radiation also damages surfaces other than human skin; for example, painted surfaces which are exposed to the sun. Zinc oxide or titanium dioxide have been used in paints to provide color and protection from damaging UV rays.

Prior art disclosures of metal oxides include preparations of spherical zinc or titanium oxide particles (U.S. Pat. No. 5,032,390, EP0 433 086 A1, U.S. Pat. Nos. 4,606,869, 3,397,257, 4,543,341, 4,808,398, 2,898,191, 4,9233,518, and 4,721,610), crystalline metal oxides (U.S. Pat. Nos. 5,093,099, 5,091,765, 4,261,965, 2,900,244, and 4,722,763), including crystalline whisker-shaped zinc oxide (U.S. Pat. No. 5,066,475), and needle-shaped zinc oxide particles (U.S. Pat. No. 5,102,650). U.S. Pat. No. 5,032,390 relates to a sunscreen composition containing from 1-25% by weight zinc oxide particles ranging in size from 70-300 μm and having a spherical shape. U.S. Pat. No. 5,093,099 relates to a process for preparing flaky fine particles of zinc oxide for external use and having an average particle diameter of 0.1-1 micron, an average thickness of 0.01-0.2 micron, and an aspect ratio of at least 3. U.S. Pat. No. 5,066,475 relates to whiskers of zinc oxide having a crystal structure which includes a central body and four needle crystal projections radially extending therefrom, and is useful in reinforcing materials. U.S. Pat. No. 5,012,650 relates to needle-like electrically conductive zinc oxide filler which is useful for its low specific volume resistance and electrical conductivity.

It is an object of the invention to provide a composition for coating a surface which contains zinc oxide particles of dimensions which allow the particles to form a highly UV-protective coating. Zinc oxide particles of the invention, because they are rod-shaped, may assume a side-by-side arrangement or a criss-cross-packing arrangement, once the surface is coated with the composition, such that there are relatively few gaps between the particles for UV rays to penetrate. It is also an object of the invention to provide a UV protectant comprising zinc oxide particles which has a high ratio of surface area to volume or weight. It is another object of the invention to provide a composition for coating a surface which possesses even spreadability over the surface. It is another object of the invention to provide a composition containing zinc oxide particles for coating a surface which possesses a smooth texture and in which the particles are easily admixed with and dispersed within a spreadable vehicle. Further, it is an object of the invention to provide a highly UV protective surface coating which is transparent, white, or of a color other than white.

SUMMARY OF THE INVENTION

The invention is based on the recognition that substantially rod-shaped zinc oxide particles are useful in a composition for application to a surface to protect the surface from ultra-violet radiation. The composition is thus capable of forming a substantially UV-impervious layer on the surface to which it is applied. As used herein, "substantially rod shape" refers to an elongated spherical shape, e.g., having an aspect ratio (i.e., length/diameter) of at least two, or a flattened rod-shape, such as the shape of a green bean.

In preferred embodiments, the composition is applicable to the surface of human skin, or to inert surfaces such as wood, plastic, plaster, metal, etc. As used herein, "inert" means inactive or inanimate. Thus, the composition may further include surface-spreadable agents which, when combined with the zinc oxide rods, allows for easy and even spreading of the rod composition onto a surface; surface-spreadable agents include emollients for spreading on the skin, or agents for spreading on inert surfaces, such as oil or latex-based paints, stains, resins, glazings, inks, glues, caulkings, etc. Examples of emollients are those found in sunscreens or cosmetics, e.g., silicone oils or mineral oils. The composition containing the substantially rod shaped particles is evenly spreadable upon the skin due to the tendency of the rod shaped particles to lie side-by-side on the skin surface and fill in the irregularities of the skin surface.

Other preferred embodiments include the following. The rod shaped particles may have a substantially spherical cross-section with an aspect ratio of at least two and preferably three. "Substantially spherical cross-section" refers to a spherical or flattened spherical cross-section. The zinc oxide particles of the invention may comprise from 0.1% to as much as 50% of the composition by weight, depending upon the desired thickness and color of the composition. More preferably, the zinc oxide rods comprise between 1% and 30% of the composition; most preferably, between 5% and 20%.

Rod-shaped particles of the invention may have a length of between 3 nanometers and 10,500 nanometers; preferably between 50 and 6,000 nanometers; more preferably between 100 and 500 nanometers, inclusive. The rod-shaped particles have a diameter of between 1 nanometer and 3,500 nanometers; preferably between 10 and 2,000 nanometers; more preferably between 33 and 200 nanometers; most preferably between 100 and 150 nanometers inclusive. In order to be useful in compositions of the invention, these rod-shaped zinc oxide particles must have an aspect ratio of at least 2; more preferably, an aspect ratio of at least 2.5; and most preferably, an aspect ratio of at least 3. Zinc oxide compositions of the invention may be formulated so as to be transparent enough to be useful in, e.g., sunscreens, cosmetics, or paints in which a natural or transparent quality is desired. A transparent quality is obtained by including in the composition small rod-shaped particles, i.e., having a length of less than 300 nm and a diameter of less than 100 nm. Larger particles, i.e., having a length longer than 300 nm and a diameter greater than 100 nm, are useful for compositions in which the opacity of the zinc oxide is an asset, e.g., white sunscreens, or white or colored particles.

Zinc oxide particles which are not rod-shaped tend to aggregate and clump upon spreading of the composition over a surface. This, in turn, dramatically reduces the sun-protecting ability of a fluid containing such particles. Some areas, e.g., beneath the clumps, will be well-protected from the UV rays and other areas, e.g., containing no surface layer of zinc oxide particles due to clumping, will be exposed to UV rays. It is preferable that the sun-protecting ability of a composition does not substantially diminish upon spreading of the composition on the surface. This may be achieved by including substantially rod-shaped zinc oxide particles in a topical application. Preferably, a composition of the invention includes a sun protection factor (SPF) of at least two. Preferably, this SPF is evenly applicable upon spreading of the composition on the skin. More preferably, the sun protection factor is at least fifteen or at least twenty-five, and most preferably, the sun protection factor is at least forty. "Evenly applicable", as used herein, is intended to mean that the composition is applicable to the surface so that UV-protection is even across the surface. For example, an SPF of forty may confer even protection across a surface against approximately 97% of the UV rays found in natural sunlight; an SPF of thirty may confer even protection across a surface against at least 95% of the UV rays; an SPF of fifteen against at least 90% of the UV rays; an SPF of ten against at least 80% of UV rays; and an SPF of two against at least 40% of UV rays.

The invention also encompasses a method of protecting a surface from the harmful effects of ultraviolet radiation, comprising applying to a surface a spreadable composition comprising zinc oxide particles having a substantially rod shape.

Preferably, according to the invention, the surface is human skin and the composition further comprises an emollient. Alternatively, the surface is inert, e.g., wood, plaster, plastic, or metal.

The invention also encompasses a method of making an ultra-violet protective composition for application to a surface, the method comprising the step of: combining zinc oxide rod-shaped particles with a surface spreadable agent to form the composition, wherein the particles are formed by bringing into contact in an aqueous solution zinc ions, ammonium ions and a carbonate source to form a precipitate, separating and optionally calcining the resultant metastable precipitate to zinc oxide particles, wherein the metastable precipitate is formed by controlling the morphology and size of the particles by maintaining, during the precipitation: a temperature between 10° to 40° C.; a pH between 5 and 10; and wherein at least one of the zinc ion and carbonate is progressively made available to the solution at a precipitation limiting rate.

Compositions of the invention include zinc oxide particles having improved weight efficiency in that their rod shape allows them to assume relative particle orientations so as to maximize their UV-absorbing properties. For example, less zinc oxide (by weight) is needed in the rod-shaped form than in the spherical form to give an equal or better sun protection factor. This is true because the attenuation of UV light by zinc oxide is largely a particle surface phenomenon which does not require much particle thickness relative to surface area. Thus, compositions of the invention provide a large surface area and require relatively less zinc oxide by weight for equivalent or better sun protection. Another advantage of compositions of the invention is that the rod shape of the particles promote a side-by-side arrangement of the rods rather than the stacking or clumping tendency of crystals or spheres. Thus, compositions of the invention provide a relatively even layer of zinc oxide, with consequent uniform UV-protection to the surface, e.g., human skin. As a result of this superior particle orientation, compositions of the present invention will more evenly cover a surface, e.g., will fill in irregularities of the human skin surface, and thus provide more even UV protection. Rod shaped zinc oxide particles do not tend to agglomerate and thus will disperse evenly within the composition. A composition of the invention thus will spread easily over the surface to which it is applied, whether the surface is animate or inanimate.

Compositions of the invention can prevent human skin from forming blotches and freckles, and may prevent rapid aging associated with exposure to UV light by scattering and absorbing UV rays and preventing sunburn and suntan. The properties of even layering of a composition of the invention and the consequent uniform UV-protection are particularly important for use in geographical areas in which exposure to UV radiation is difficult to protect against, e.g., tropical countries or areas located beneath ozone-depleted atmospheres, and also is important for use by UV-sensitive or light-skinned individuals in any geographic area. Inanimate surfaces, e.g., wood, plaster, plastic, or metal, benefit from topical application of compositions of the invention by becoming more resistant to the fading brought on by exposure to UV light.

These and other properties of the invention will be understood by those skilled in the art from the description herein and from the claims.

DESCRIPTION

Drawings

PREFERRED EMBODIMENTS

Figure 1:
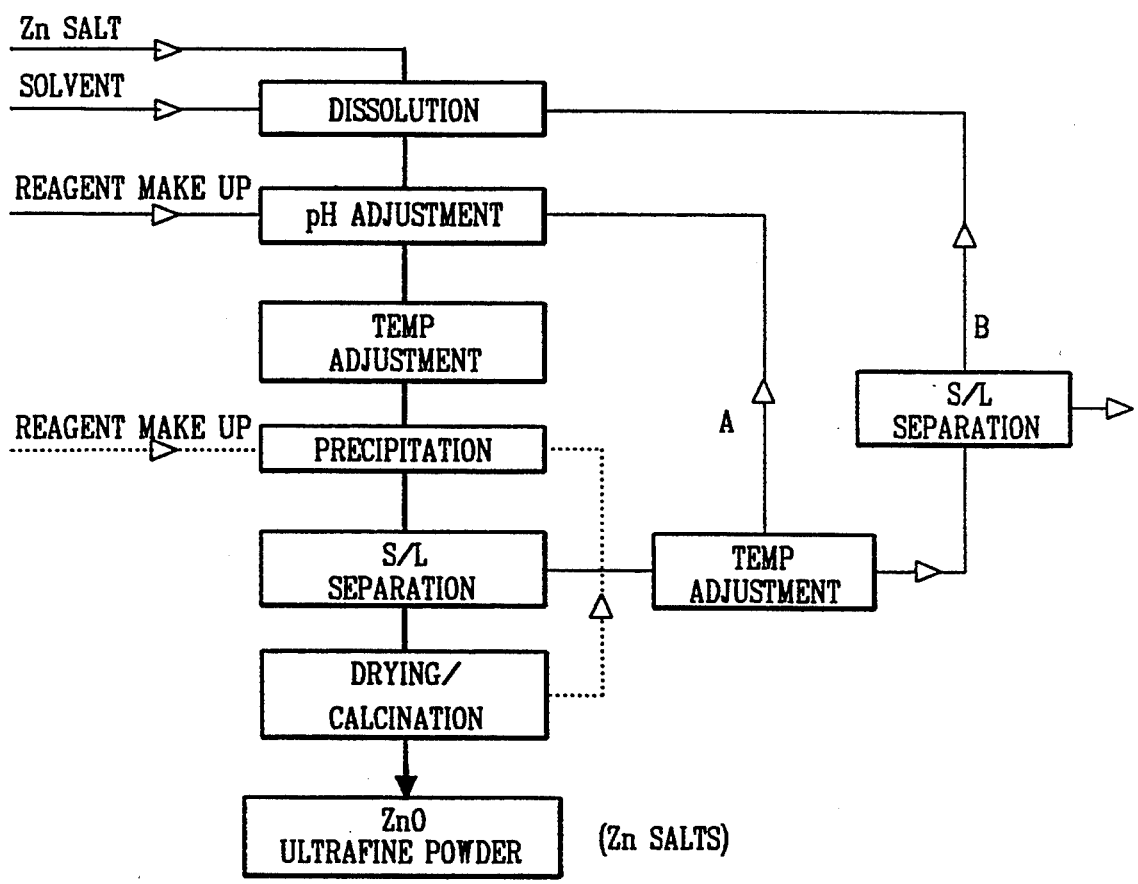
FIG. 1 is a flow diagram of a first process for producing the zinc oxide particles described herein.

Described below are ultrafine zinc oxide, carbonates and oxalates with defined particle morphologies, and techniques for the production of such defined-morphology-particles which avoid the deficiencies of the prior art calcination or decomposition steps, and which are amenable to simultaneous or sequential co-precipitant doping.

Zinc oxide particles in the form of rods in the size range 30 to 500 and even up to 10,500 nm in length, between 1 and 3,500 nm, preferably between 10 and 2,000 nm, more preferably 100 and 150 nm and 10 to 150 nm in diameter, are most useful in the invention. The rods and fibers will generally have a circular cross section and comprise X-ray amorphous material.

Typically, the particles will display a very homogenous size and aspect ratio distribution with micrographs of the rods showing greater than 75% and even up to 90% of the particles having a substantially similar size and aspect ratio. For instance, within a rod population of nominal aspect ratio 3 and diameter 100 nm, it is possible to produce populations in which 75% of the particles fall within an aspect ratio range of 2–4 and diameter range 50 to 150 nm which represents outstanding homogeneity in comparison to prior art methods.

Such zinc oxide particles with defined sizes and morphologies, including those produced by the techniques below, show interesting rheological properties. The rheological properties of the particles assure enhanced dispersability within the topical composition, e.g., sunscreen, paint, etc., substrate.

Also described herein in detail is a method for the production of ultrafine zinc precipitates in which zinc ions, ammonium ions and a carbonate source are brought into mutual contact in an aqueous solution to form a precipitate, the resulting precipitate is separated and optionally calcined to zinc oxide, wherein the metastable precipitate is formed by controlling the morphology and size of the particles by maintaining, during precipitation: a temperature between 10° and 40° C., preferably 15° to 30° C. and more preferably 20° to 22° C.; a pH between 5 and 10; and wherein at least one of the zinc ion and carbonate source is progressively made available to the solution at a precipitation limiting rate.

The above-defined method is in contrast to prior art methods in which a high pH solution of all the precipitant ions (with the zinc as zincate) is caused to precipitate by lowering of the pH. The present invention avoids the production of undesirable high pH artifacts such as microprecipitates of ZnOH, which can act as seeds for the uncontrolled growth of zinc carbonate complexes, by initially setting the pH of the mother liquor. In this fashion, high quality, substantially uniform metastable complexes can be reproduceably precipitated with sizes and morphologies which possess interesting rheological properties.

Zinc oxide particles produced according to the procedure described herein are ultrafine precipitates of controlled size and morphology produced by the above method and defining substantially homogeneous populations of spheres, rods or fibers with a narrow diameter and aspect ratio distribution.

The precipitate which forms as a metastable mixed complex of zinc, or zinc and some other cation such as ammonium or a dopant, and hydroxy, bicarbonate, carbonate or oxalate, etc., may be recovered as the salt by conventional techniques or alternatively must be calcined to produce zinc oxide particles. The calcination temperature will depend to some extent on the exact nature of the carbonate moiety but the metastable nature of the precipitate will generally allow the use of comparatively low calcination temperatures in comparison with classic carbonate decomposition. For instance, calcination temperatures as low as 250°–340° C., perhaps even 200° C. are achievable in comparison to the 400°–800° C. required in classic carbonate calcinations. Oxalates and other bicarboxylate metastable precipitates may even require lower calcination temperatures, such as 120° C.

The precipitates formed by the procedures described herein are metastable and therefore prolonged contact with the chemically reactive environment of the mother liquor will tend to cause maturing or ripening. Prior to physical separation of the precipitate, it can be isolated, to some extent, from its chemical environment. For instance, manipulation of the dissolved carbon dioxide concentration can delay ripening in solution, prior to filtration or centrifugal separation. The precipitates are not water sensitive, unlike the prior art zincate precipitation techniques of, e.g., U.S. Pat. No. 5,132,104, which require washing of the separated precipitate in polar organic solvents such as acetone or ethanol.

Suitable separation techniques can include an initial surface charge neutralization step of coating the surface of the precipitate suspension with a surfactant such as methacorylate followed by spray-drying. Calcination of the resultant particles will tend to volatilise any surfactant residues remaining after the spray drying operation.

Spray roasting, in which the precipitate containing solution is sprayed into a heated chamber at temperatures approaching 270° C. can simultaneously affect dewatering and calcination. Filtration, leading to a more densely packed arrangement can also be used, optionally in conjunction with surfactant based redispersion techniques.

The expression 'carbonate source' includes carbonates, bicarbonates, oxalates, malates, succinates and also carbon dioxide introduced into the aqueous solution as a gaseous phase or evolved in situ through dissolution or decomposition. Ammonium salts are preferred especially when the resultant zinc oxide is intended for applications in which metal ion contamination should be avoided, such as dermal sunscreens and electrostatic applications.

Preferred zinc salts to produce the aqueous zinc solution include the nitrate, sulfate and chloride. The solution may be pure water or a mixture of water and another miscible or immiscible solvent such as an alcohol or acetonitrile.

Control of the relative availability of carbonate to zinc ion concentration within the aqueous solution can be simply achieved by the gradual addition of the carbonate source and/or zinc ion, in solid but preferably dissolved form, to the aqueous mother liquor. Alternatively, the reagents can be added in a form which decomposes to release and make available zinc ion or the carbonate source. For example, urea or ammonium carbamate can release carbon dioxide in a retarded fashion to ensure a suitably low reactive concentration. Metal chelators such as the EDTA family can maintain a low reactive zinc ion concentration in the aqueous solution. When carbon dioxide is used as the carbonate source it is convenient to bubble it through the aqueous solution, optionally in conjunction with a solubility regulator such as ammonia.

Control of the pH within the above defined range is advantageously carried out with dilute reagents such as 0.05 to 0.25M KOH or NaOH, in conjunction with vigorous mixing. The preferred pH control agent is ammonium hydroxide, such as a 5–10% ammonia in distilled water solution. The ratio of ammonium to carbonate source will generally be lower, for instance approaching unity compared with prior art methods, which may lead to enhanced metastability in the precipitated complexes.

Appropriate control of the relative availability of the various ions allows control of the aspect ratio of the resultant precipitant. Generally speaking, within the above-defined process conditions, the slower the rate of reactant addition, the greater is the aspect ratio, i.e. the length of the rods or fibers. Conversely, increasing the addition rate will decrease the aspect ratio; however, too rapid an addition will lead to the non-homogenous particle size distributions displayed by prior art techniques. Addition rates will vary with the strength and solubility of the reagents, but as a guide, for a 0.5 molar concentration of zinc ion, an addition rate between 0.5 and 2.0 liters/hour for a 0.4 molar equivalent carbonate source has been workable. It should, of course, be recognized that the hydrodynamics of the solution influence the intended morphology. In particular, in contrast to conventional crystal deposition techniques, high aspect ratios will demand effective mixing, even with relatively dilute reagents to avoid localized regions of aberrant reactant concentration.

The actual hydrodynamic conditions employed during precipitation will depend on reactor size, geometry, number of baffles, etc., but generally speaking will be as high as possible without inducing cavitation or other admission of air bubbles into the system. As a guide, a Reynolds number of at least some hundreds, preferably 8000 and above, will be appropriate for many systems.

The process for making zinc oxide rods allows doping of the zinc precipitate complex and any zinc oxide end products through co-precipitation of the zinc precipitate with a dopant such as yttrium, aluminum, gallium, platinum, bismuth, a lanthanide, curium, molybdenum, nickel, cobalt, antimony, chromium or other group III–VII compound. Doping may increase the UV absorbance properties of the rods. Typically 0.01 to 10% of the resultant particles will comprise the dopant oxide.

Co-precipitation can be performed simultaneously with formation of the zinc oxide to produce homogenous particles. The respective concentrations of dopant oxide to zinc oxide in the end product can be controlled through adjustment of their respective reagent concentrations during precipitation.

Alternatively, doping can be performed sequentially by first forming a zinc carbonate core and then precipitating one or more layers of dopant over the core. The end product powders will then have the dopant on the zinc interface with very little solubility in the solid phase.

Preparation of Zinc Oxide Particles

Zinc oxide rods are made by carefully controlled agglomeration of spherical particles, prepared as described above.

Referring initially to FIG. 1, this procedure includes the steps of forming an aqueous solution of a zinc ion, followed by pH and temperature adjustment. A gaseous carbon dioxide stream is introduced to the zinc solution while a pH and temperature feedback loop maintains precise control over the reaction environment. A precipitate comprising a mixed complex of zinc and hydroxide, bicarbonate and carbonate forms as the carbon dioxide is fed in. The metastable precipitate is separated from the mother liquor which is temperature treated to reform the reagents. The precipitate can be low temperature calcined to form an ultrafine ZnO powder of defined particle size and morphology to form a mixed complex of zinc and hydroxides, bicarbonates and carbonate.

In this procedure, the reactor comprises a 2 liter cylinder equipped with vertically extending baffles around its circumference. Stirring was achieved with a central impeller which was speed governed to within 1% of the nominal rpm. Reagent addition to the reactor was via glass conduits opening into the reactor adjacent the impeller, thereby assuring instant mixing. Gaseous reagents were added via microporous sintered glass tips again adjacent the impeller.

A central microprocessor received input form pH, temperature and ion-selective probes mounted in the reactor and controlled peristaltic reagent input pumps and high precision reagent input valves. Bulk reagent vessels were equilibrated to the intended reaction temperature.

68.14 g of 99.81% pure ZnCl (Sigma Chemical Co., St. Louis, Mo.; Aldrich Chemical Co., Milwaukee, Wis.) was dissolved in 1.5 liters of distilled water and fed into the reactor. The temperature was reduced to 22° C. and maintained within a degree of this temperature, throughout the experiment. Stirring was set to 175 rpm. The pH was controlled with an ammonium solution comprising 8% ammonia in distilled water which was very gradually added to the stirred solution so as to avoid localized pH perturbation. The pH was maintained in this fashion within the range 9.5–10 throughout the experiment.

A carbonate source comprising carbon dioxide gas 0.1% (balance oxygen and nitrogen) was introduced to the solution at approximately 4.0 l/h. The precipitate formed instantly and the carbon dioxide inflow was continued until an appreciable amount of precipitate was dispersed in the reactor.

The precipitate was washed in distilled water and dried. The powder was X-ray amorphous. The powder was calcined at 270° C. for 3 hours to form a white powder of submicron particles with a narrow size distribution and with a density of around 5.6 g/cm and surface area of 35 m/g.

Figure 2:
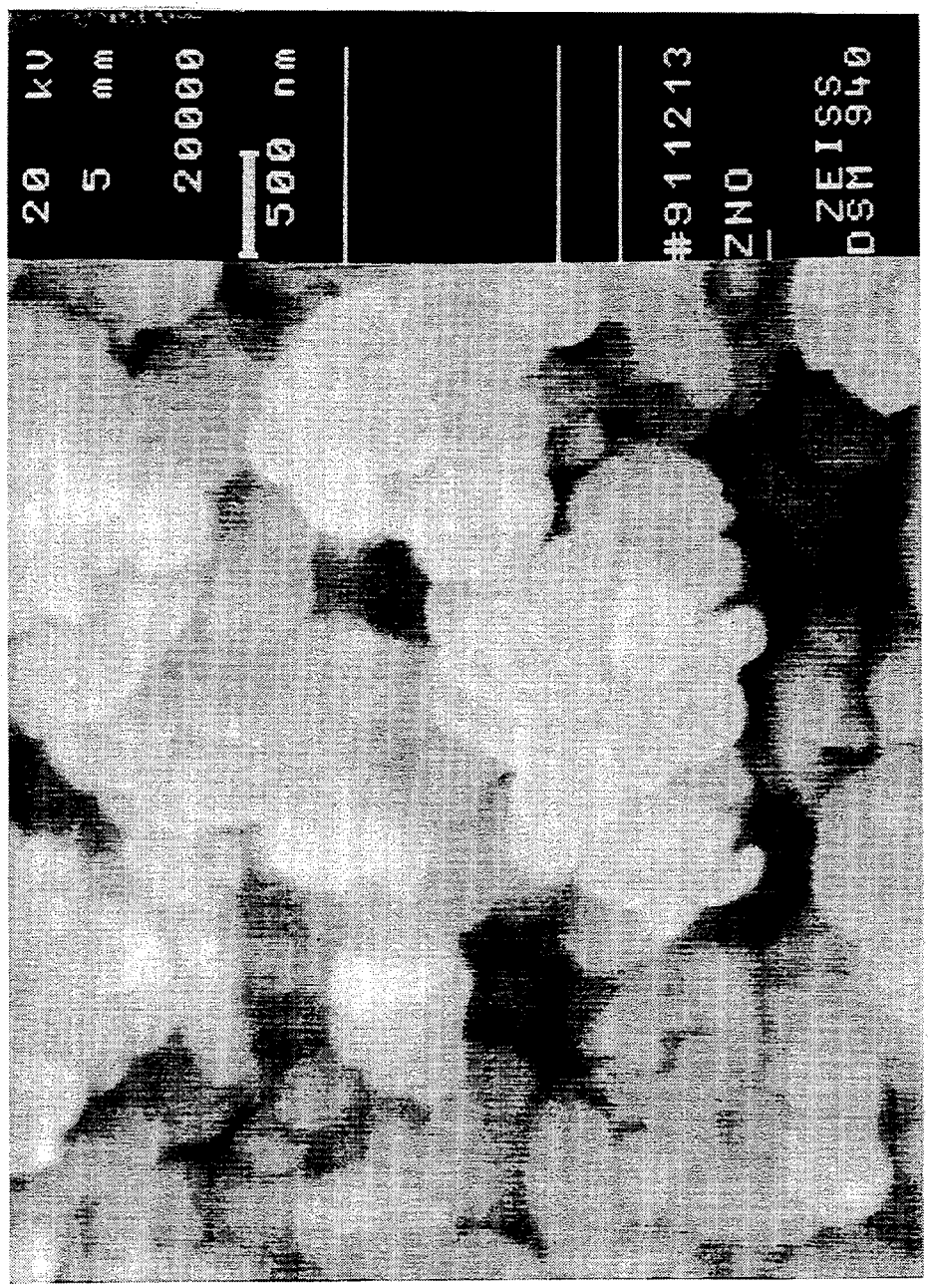
FIG. 2 is a scanning electron micrograph of spherically shaped zinc oxide particles.

The powder was prepared for scanning electron microscopy by the gold coating method. As can be seen from the micrograph of FIG. 2, these process conditions produced a sphere morphology with a diameter between 50 and 150 nm.

Referring once again to FIG. 1, process refinements can include the recycling of the ammonia component, heat separated from the mother liquor after removal of the precipitate, back to the pH adjustment step, marked with the letter A in FIG. 1. Additionally or alternatively, the liquid from this ammonia recovery step can be treated to recover the solvent which can also be recycled to provide a virtually closed environmentally friendly system ("B" in FIG. 1).

Preparation of Shorter Zinc Oxide Particles

Figure 3:
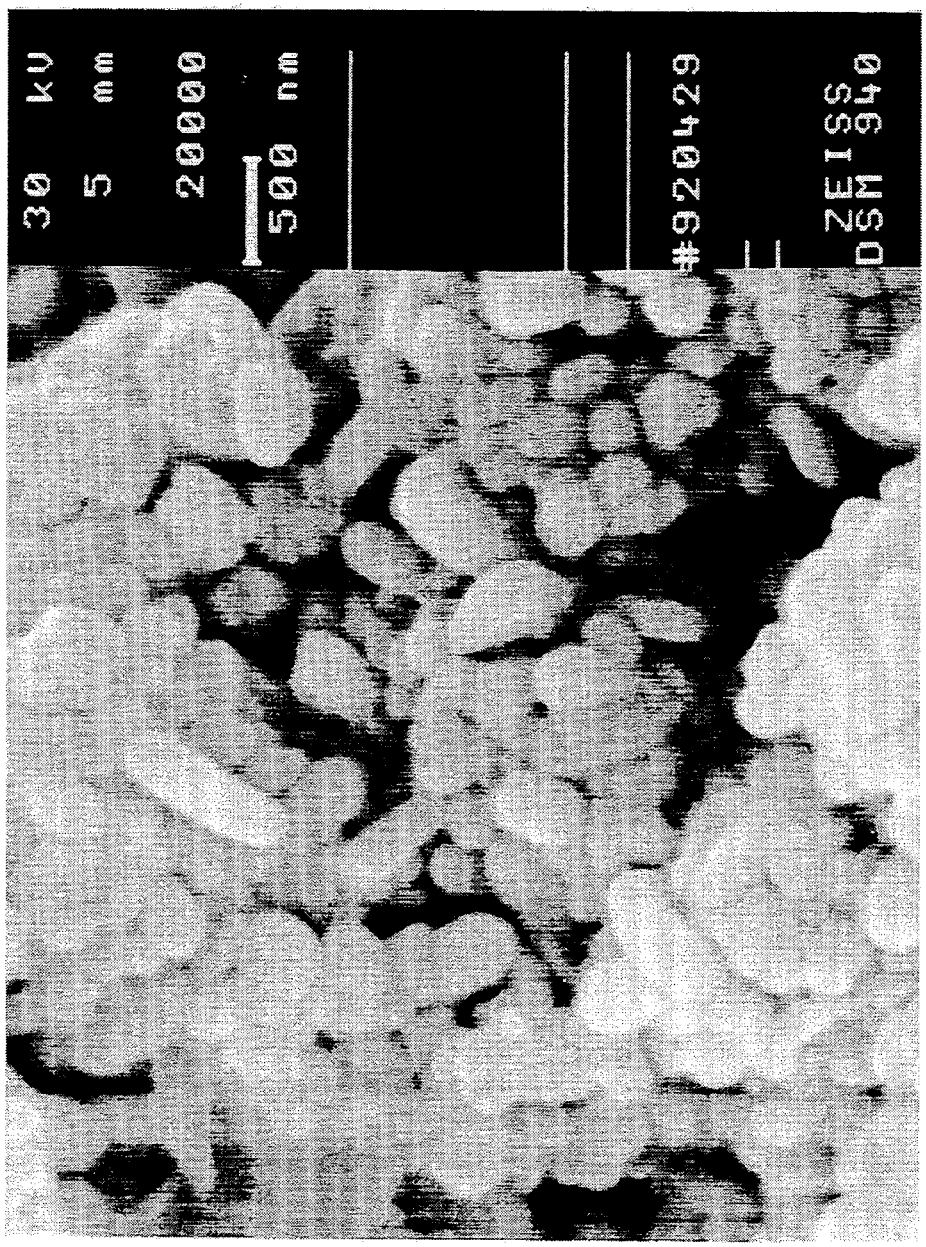
FIG. 3 is a scanning electron micrograph of rod shaped zinc oxide particles.

To obtain rod-shaped particles, as shown in FIG. 3, the apparatus described above was charged with 1.5 l of distilled water. Stirring, temperature and pH control were also as above.

Aqueous 0.3M zinc chloride and 0.2M ammonium bicarbonate solutions were simultaneously added to the reactor via separate conduits at a respective rate of 0.5 l/h and 0.5 l/h. The resultant precipitate was separated as above.

Calcination of the resultant precipitate was at 250° C. for 3 hours. FIG. 3 shows the resultant zinc oxide particles which display a rod morphology with diameters between 50 to 100 nm and lengths between 100 to 200 nm.

When carbon dioxide is used as the precipitant, an additional recycling possibility is to collect carbon dioxide from the calcination step for use as the precipitant, as shown with dotted lines on FIG. 1.

Preparation of Longer Zinc Oxide Particles

Longer zinc oxide rods may be prepared as follows. In the system described for the preparation of zinc oxide rods, but with a stirring speed of 200 to 250 rpm, 0.3M zinc chloride and 0.1M carbamate solutions were simultaneously added to the reactor through respective glass conduits at respective addition rates of 0.5 and 0.7 l/h. Carbamate is stable in solution but breaks down via metal catalysis to liberate reactively available carbon dioxide and ammonia in solution.

Figure 4:
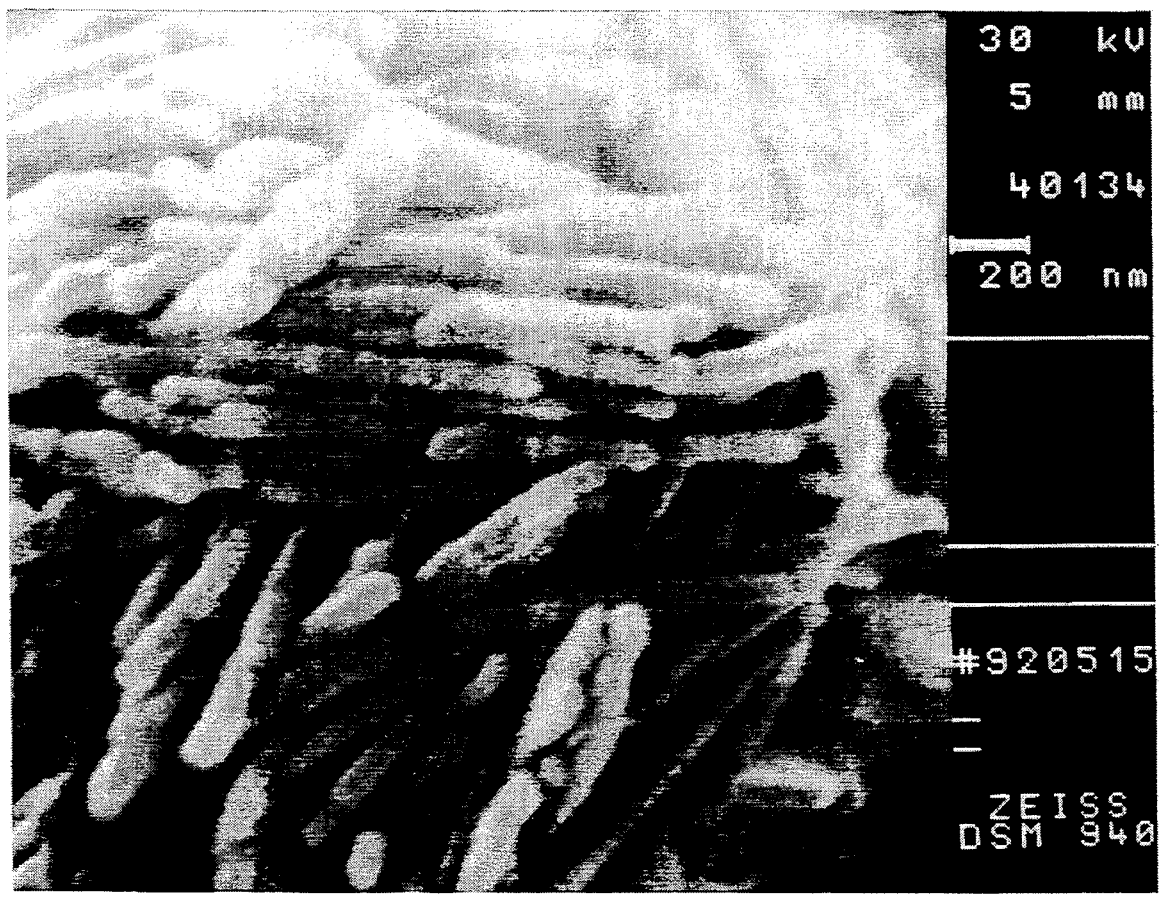
FIG. 4 is a scanning electron micrograph of fiber shaped zinc oxide particles.

The resultant precipitate was separated and prepared for SEM as above. These process conditions produced a longer zinc oxide rod morphology, as shown in the micrograph in FIG. 4. The rods display an homogenous size distribution between 10 to 50 nm in diameter and 50 to 500 nm in length.

Preparation of Zinc Oxide via Oxalate Route

In the reactor conditions described above in preparation of the shorter zinc oxide rods, but with the stirring speed within 150 to 175 rpm, 0.2M zinc chloride and 0.1M oxalic acid were simultaneously added to the reactor at respective rates 0.5 and 0.8 l/h. The precipitate was recovered as described in the rod preparation above, but at a calcination temperature of 125° C. Electron microscopy of the resultant powder showed spherical particles with diameters within the range 50 to 150 nm. Rod morphologies can also be deposited using this reagent system.

Preparation of Doped Zinc Oxide particles

Figure 5:
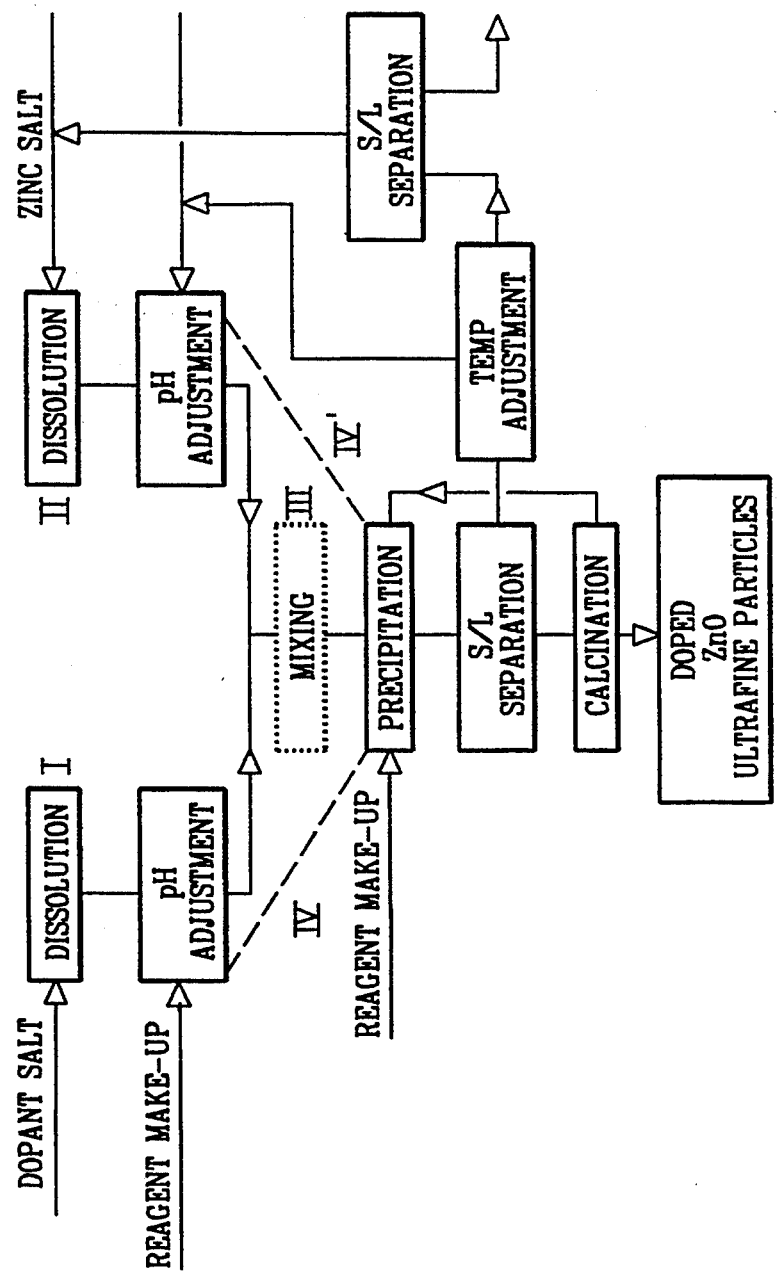
FIG. 5 is a flow diagram of a second process for producing zinc oxide particles as described herein.

Referring now to FIG. 5, a scheme for the production of doped zinc oxide particles is shown. In this scheme, two separate metal solutions, the first a zinc ion solution (I, at the top, left) and the second a dopant metal ion solution (II, top, right) are prepared and separately pH and temperature adjusted.

In a first process variant leading to an homogenous dopant/zinc precipitate, the respective metal ion solutions are mixed (III) and introduced to the mother liquor together. In this fashion, the resultant precipitate complex comprises an intimate coprecipitate of dopant and zinc, the proportion of each reflecting their respective concentrations in the mixed input stream. As with the earlier described procedures, pH and temperature feedback loops (IV, IV') can be provided to maintain optional reaction conditions during the precipitation, in particular when it is desired to take account of the differing solubilities of zinc and dopant metal ions at different pHs to assist in regulating proportionality of deposition of the respective metals.

In a second process variant, the mixing of metal ion solutions I and II is avoided and the respective solutions are admitted to the reactor sequentially. The resultant precipitate comprises an initially precipitated zinc complex core surrounded by a layer of dopant ion complex. Again, the pH control of the respective metal solutions may take advantage of the differing solubilities of the respective metals at different acidities.

In each case, the respective precipitates are separated and calcined in similar fashion to the above described procedures to produce doped ZnO particles of defined size and morphology.

Preparation of Zn/Bi Coprecipitate

A first process variant of the preparation of doped zinc oxide particles was used to produce a mixed coprecipitate of metastable Zn and Bi carbonates.

The reactor system described above in the preparation of zinc oxide particles, as shown in FIGS. 1 and 5, was charged with distilled water and the pH initially adjusted to 8–11 with dilute ammonia solution. A first solution was prepared by mixing 0.3M $ZnCl_2$ and 0.01M $Bi(NO_3)_3$ in the ratio 3:1, the ratio being adjusted with reference to the desired composition of the end product oxide. A second solution comprised 0.1M $NH_4HCO_3$.

The first and second solutions were added dropwise to the aqueous system and the pH carefully maintained at the initial value by dropwise addition of the dilute ammonia solution during vigourous agitation. A composite consisting essentially of metastable zinc and bismuth carbonates was coprecipititated and calcined to obtain a very homogenous mixture of ZnO and $Bi_2O_3$ having the above defined particle size and distribution.

A variant of this process uses a dual dopant oxide solution, in particular with a solution of Bi and Sb to produce a trimetal coprecipitate.

Preparation of $ZnO/Al_2O_3$ Coprecipitate

A second process variant of FIG. 5 was used to produce a coprecipitate of ZnO and $Al_2O_3$ suitable for electronic applications.

The water charged reactor system described in the above description of the preparation of zinc oxide particles was pH adjusted to between 8 and 10. With reference to FIG. 5, a zinc core precipitate was first produced by dropwise addition of a solution II consisting of 0.3M $ZnCl_2$ and a separate carbonate source solution comprising 0.1M $NH_4HCO_3$. The pH was controlled via the feedback loop with small additions of dilute ammonia to the vigourously agitated aqueous solution.

Referring again to FIG. 5, solution I comprised 0.1M $AlNO_3$ which was subsequently precipitated onto the suspended zinc precipitate core. Calcination of the mixed precipitate provided a uniform powder of biphase aluminium oxide on zinc oxide appropriate for semiconducting roles, for example, conventional compression sintering to form varistors.

This reagent system can also be used in the process variant of the Zn/Bi coprecipitate preparation described above, for example, at a 5:1 ratio of the Zn:Al solutions to form a homogenous coprecipitate.

Formulations

Zinc oxide particles contained in compositions of the invention have a length to diameter ratio of at least two and preferably three and have dimensions within the range of 3–10,500 nm length and 1–3,500 nm diameter. Within this range, the size of the zinc oxide rod will depend upon the type of surface to which the composition of the invention is to be applied and whether transparent or opaque compositions are desired.

1. Transparent Compositions

Smaller rods are useful for compositions which are transparent, e.g., some sunscreens and cosmetics, or clear paints. Rods having a length of less than 300 nm and a diameter of less than 100 nm are optimal smaller rods to confer transparency to the composition. An example of such a composition is a sunscreen, several formulations of which are provided below.

Any component which is found in conventional sunscreens may be used in a sunscreen formulation in compositions of the invention. Furthermore, the zinc oxide rods in compositions of the invention may be combined with other metal oxides, e.g., titanium oxides, as described in U.S. Pat. No. 5,032,390. For example, a mixture of zinc oxide rods and titanium oxide particles, e.g., of a generally spherical or acicular shape may be useful in a sunscreen, cosmetic, or paint composition of the invention. Other components useful in compositions of the invention include organic sunscreens, inorganic sunscreens, thickeners, emulsifiers, fragrances, waterproofing agents, or components found in cosmetics.

Zinc oxide rods may be surface modified in order to make them more compatible in a given formulation. For example, the surface of a zinc oxide particle may be treated with silicone-like compounds in order to increase its compatibility with oil-based compositions. See "Chemistry of Pigments and Fillers", D. H. Solomon et al., Eds., 1983, Wiley Inter-Science, hereby incorporated by reference.

Generally, sunscreen lotions contain water, emulsifier, zinc and/or titanium oxides, and a UVB absorber.

|  | % BY WEIGHT |
|---|---|
| Phase A | |
| DEIONIZED WATER | 52.00 |
| NACL (20% SOLN) | 2.50 |
| GERMABEN II | 1.00 |
| Phase B | |
| ZINC OXIDE RODS | 5.00 |
| OCTYL METHOXYCINNAMATE | 7.50 |
| DIMETHICONE SF 96-5 | 5.00 |
| DC 344 FLUID | 21.00 |
| Q2-1401 | 1.00 |
| ABIL EM90 | 5.00 |
|  | 100.00 |

The above sunscreen formulation is prepared by mixing phases A and B, preferably under propellar agitation. The mixed phases are then thoroughly homogenized, and then packaged in an appropriate container.

Another representative sunscreen formulation contains a water/oil emulsion, and is estimated to have an SPF of 20. This composition of the invention includes 7.5% by weight zinc oxide rod shaped particles. The size of the rod shaped particles useful in this type of sunscreen may be, for example, 200 nm in length and 50 nm in diameter.

| NO. | PHASE | INGREDIENT | % BY WEIGHT | BATCH SIZE 500.00 | BATCH SIZE 1500.00 |
|---|---|---|---|---|---|
| 1 | A | DEIONIZED WATER | 54.90 | 274.50 | 823.50 |
| 2 | A | PROPYLENE GLYCOL | 3.00 | 15.00 | 45.00 |
| 3 | A | NA4EDTA | 0.10 | 0.50 | 1.50 |
| 4 | A | KELTROL T | 0.50 | 2.50 | 7.50 |
| 5 | B | FINSOLV TN | 5.00 | 25.00 | 75.00 |
| 6 | B | MICROFINE TITANIUM DIOXIDE | 7.50 | 37.50 | 112.50 |
| 7 | B | ARLACEL 165 | 4.00 | 20.00 | 60.00 |
| 8 | B | VITAMIN E ACETATE | 0.25 | 1.25 | 3.75 |
| 5 | B | IPM | 5.00 | 25.00 | 75.00 |
| 6 | B | GANEX V 216 | 3.00 | 15.00 | 45.00 |
| 7 | B | ZINC OXIDE RODS | 7.50 | 37.50 | 112.50 |
| 8 | B | DC 344 FLUID | 3.00 | 15.00 | 45.00 |
| 9 | B | PROMULGEN D | 3.00 | 15.00 | 45.00 |
| 10 | B | MINERAL OIL (CARNATION) | 2.00 | 10.00 | 30.00 |
| 11 | C | GERMABEN II | 1.00 | 5.00 | 15.00 |
| 12 | D | PERFUME IFF 1750-IS | 0.25 | 1.25 | 3.75 |
|  |  |  | 100.00 | 500.00 | 1500.00 |

Sunscreen creams may contain less water and a thicker emulsifier, e.g., bee wax. The preparation and formulation of both sunscreen lotions and creams is well-known in the art. A typical sunscreen lotion contains a water/silicone emulsion which imparts a water-proof quality and thus prevents easy removal of the sunscreen from the skin. A sunscreen may be a combination sunscreen, i.e., containing two sunscreen components, 5% by weight zinc oxide rod-shaped particles, and an organic sunscreen (octyl methoxycinnamate) which absorbs UV light in the UVB range. If a noncombination, i.e., zinc oxide-only, sunscreen is desired, the organic sunscreen may be eliminated from the formulation and replaced with an equal percentage by weight of water. The size of the zinc oxide rods useful in the following sunscreen may be, for example, 250 nm length and 75 nm diameter. Even smaller rod shaped particles may be used if a completely transparent sunscreen is desired. The following sunscreen formulation is a representative combination sunscreen composition containing zinc oxide rods, and is estimated to have an SPF of 15.7.

The formulation is prepared by heating Phase A to 75° C. and Phase B to 75° C. Phase B is then added to Phase A and mixed, and together they are cooled to 45° C. before Phase C is added and mixed. Phases A, B, and C are then homogenized and packaged.

2. Opaque Compositions

Compositions of the invention may be opaque, e.g., a white or colored cosmetic or paint. An opaque sunscreen may be prepared as described above for transparent sunscreens, but will contain larger rods. White or colored cosmetics are prepared by mixing any conventional formulation with larger zinc oxide rods. Larger rods, i.e., those capable of conferring opacity to a composition of the invention, are particles having a length longer than 300 nm and a diameter greater than 100 nm.

In cosmetic compositions of the invention, the zinc oxide rods are combined with a cosmetic carrier. The particles may be combined with foundations by including loading pigment, coloring pigment, oil and shaping agent; creams by including oil, water, and emulsifier; lotions by including oil, water, solubilizing agent and lower alcohol; and lipsticks by including oil and colorant. Examples of zinc oxide rods contained in cosmetic compositions having a creamy foundation and an oily foundation follow.

A creamy foundation composition of the invention may comprise the following components:

| Composition | |
|---|---|
| (1) stearic acid | 5 wt. % |
| (2) lipophilic glycerol monostearate | 2.5 |
| (3) cetostearyl alcohol | 1 |
| (4) propylene glycol monolaurate | 3 |
| (5) squalane | 7 |
| (6) olive oil | 8 |
| (7) purified water | the balance |
| (8) antiseptic | a suitable amount |
| (9) triethanolamine | 1.2 |
| (10) sorbitol | 3 |
| (11) titanium oxide | 10 |
| (12) talc | 5 |
| (13) coloring pigment | a suitable amount |
| (14) zinc oxide rods | 8 |
| (15) perfume | a minute amount |

This creamy foundation can be prepared as follows. Components (11) to (14) are mixed together and pulverized. The zinc oxide rods (14) useful in this type of composition may be, for example, 400 nm length and 100 nm diameter. Separately, aqueous components (7) to (10) are mixed together to form a solution. The pulverized pigment mixture is dispersed in the solution and a dispersion thus formed is heated to 75° C. A mixture of oily components (1) to (6) is heated to 80° C. to form a solution, which is added to the aqueous dispersion prepared as above under stirring to form an emulsion. The emulsion is cooled under stirring to 50° C. and component (15) is added thereto. The mixture is cooled under stirring.

An example of an oily cosmetic foundation comprising zinc oxide rods follows.

| Composition | |
|---|---|
| (1) zinc oxide rods | 10 wt. % |
| (2) talc | the balance |
| (3) kaolin | 12 |
| (4) titanium oxide | 13 |
| (5) red iron oxide | 1.5 |
| (6) yellow iron oxide | 2.0 |
| (7) black iron oxide | 0.5 |
| (8) liquid paraffin | 15 |
| (9) isopropyl palmitate | 10 |
| (10) lanolin alcohol | 3 |
| (11) microcrystalline wax | 7 |
| (12) ozocerite | 8 |
| (13) antiseptic | a suitable amount |
| (14) perfume | a suitable amount |

The oily foundation may be prepared by mixing and pulverizing components (1) to (7). The zinc oxide rods useful in this preparation may be, for example, 475 nm length and 125 nm diameter. This mixture is slowly added to an oily solution prepared by heating components (8) to (13) at 80° C. and then is dispersed homogeneously. Component (14) is added to the dispersion and the mixture thus formed is packed in a metallic pan and cooled.

An opaque paint may be prepared from rod-shaped zinc oxide particles by mixing the larger zinc oxide rods with any type of commercially available paint, using enough zinc oxide to impart the desired color. For example, 10% by weight zinc oxide rods of, for example, 450 nm length and 150 nm diameter are combined with the commercial paint.

Other examples of bases with which zinc oxide rods may be added include wood stains, sealers, caulking, roof shingles, automobile clear coats, glass coatings, UV-protective coatings for eyeglasses, varnishes, and fabric protectants.

Zinc oxide rods described herein may be included in a paint or similar polymer, or base having the particles incorporated therein, typically in an amount corresponding to 0.01 to 50 wt %. Higher aspect ratios are generally preferred to enhance interparticle contact and thereby UV absorbance. The elongate shape and ultrafine size of the present particles leads to good dispersability of the particles within the substrate allowing smaller quantities of the particles to be used in comparison to prior art sunscreen, paint, or other topical compositions.

Testing

It may be desirable to test a composition of the invention for its ability to protect the surface to which it is applied from ultraviolet radiation. Testing is particularly important for a composition which is useful for application to human skin, e.g., a sunscreen. Sunscreens may be tested as described in the Federal Register, Vol. 43, No. 166, Food and Drug Administration guidelines, entitled "Sunscreen Drug Products for Over-the-counter Human Use", Part II, Aug. 25, 1978, pages 38259-38262 (hereby incorporated by reference). The testing procedure is as follows.

Sunscreen testing may be performed on human male or female volunteers. For inclusion in the test, the following criteria should be met. The subjects should be free of any dermatological or systemic disorder which would interfere with the results, e.g., no known abnormal response to sunlight, heat rash, chronic skin allergies, suntan or sunburn, etc. The subjects should not be under a doctor's care, or taking medication which may mask or interfere with the results. These determinations may be made by trained dermatological medical staff. The subjects should read, understand, and sign an informed consent document, as required by CFR Title 21, Part 20 regulations. The panel of subject volunteers should be classified as to skin type I, II or III defined according to Federal Register 43: 38260, 1978, and as follows.

Type I—Always burns easily; never tans (sensitive)

Type II—Always burns easily; tans minimally (sensitive)

Type III—Burns moderately; tans gradually (light brown—normal).

The light source employed in the test is a 150 watt Xenon Arc Solar Simulator (Berger, D. S.: Specification and design of solar ultraviolet simulators. *J. Invest. Dermatol.* 53: 192-199, 1969, Solar Light Co., Philadelphia, Pa., Model 12S, Model 14S or Model 600) having a continuous emission spectrum in the UV-B range from 290 to 320 nm. Xenon arc was selected on the basis of its black body radiation temperature of 6000° K. which produces continuous UV spectra (all wavelengths) substantially equivalent to that of natural sunlight. This device is equipped with a dichroic mirror (which reflects all radiation below 400 nm) and works in conjunction with a 1 mm thick Schott WG-320 filter (which absorbs all radiation below 290 nm) to produce simulation of the solar UVA-UVB spectrum. A 1 mm thick UG 5 or UG 11 filter (black lens) is added to remove reflected (infra-red, greater than 700 nm) heat and remaining visible radiation.

UVB radiation may be monitored continuously during exposure using a Model DCS-1 Sunburn UV Meter/Dose Controller System (Solar Light Co.), formerly known as the Robertson-Berger Sunburn meter (R-B meter). Measurements are taken at a position within 8 mm from the surface of the skin. The field of irradiation is 1 cm in diameter. Realignment of the Light Sources and calibration of the sunburn meters should be conducted at least semi-annually.

The SPF testing procedure is based on that described in the Federal Register, Vol. 43: 38264–38267, 1978. One test site area served to determine each subject's Minimal Erythema Dose (MED). This is executed by exposing the back to a series of timed incremental UV exposures at 25% intervals. The subject's smallest exposure or the least amount of energy required to produce erythema (MED) is the shortest time of exposure that produces minimally perceptible erythema at 20 to 24 hours post-irradiation. The test area is described as the infrascapular area of the back to the right and left of the midline. An 8% homosalate standard is delivered to the test site through a plastic volumetric syringe. This standard will give a uniform SPF of approximately 4–5.

The material is then evenly applied to a rectangular area measuring 5 cm × 10 cm (50 cm$^2$) for a final concentration of 2.0 mg/cm$^2$. Fifteen (15.0) minutes after application, a series of UV light exposures in 25% increments, calculated from previously determined MED's, bracketing the intended SPF is administered from the solar simulator to subsites within the treated area. On the actual day of testing, another series of exposures similar to the one given on the previous day is administered to an adjacent untreated, unprotected area of the skin to re-determine the MED. Another adjacent test site is then selected to perform an SPF determination on the test substance.

Responses are evaluated as follows. Twenty to twenty-four hours post-exposure, the volunteers are evaluated for delayed erythemic response. The smallest exposure or the least amount of energy required to produce erythema (MED) in the treated site is recorded. The SPF is then calculated according to the following equation:

SPF=MED Protected Skin/MED Unprotected Skin. Results are rejected if the responses on the treated test site are randomly absent or out of sequence. This is an indication that the products are not spread uniformly. Results also are rejected if an MED could not be obtained due to elicited response at all exposure sites. If the exposure series failed to elicit an MED response on either the untreated or the applied skin areas, the test is then considered a technical failure and the subject's data is discarded.

Testing of topical zinc oxide rod containing surface applicants for coating inanimate objects, e.g., paint on a wooden surface, may be performed using a fadeometer as a UV light source to promote fading. A fadeometer effects incremental fading of surface color under controlled lighting conditions. The surface is exposed to the light source for a given period of time, e.g., 10–60 hours, most typically 30 hours. Fading is determined either visually by eye or by measuring color reflectance in a reflectance spectrophotometer. UV protection of a surface coating for inanimate surfaces according to the invention may be defined as those zinc oxide rod-containing coatings which fade less than 70% in 60 hours, preferably, less than 80% in 60 hours, most preferably less than 95% in 60 hours.

Other Embodiments

While the invention has been described in detail and with reference to specific embodiments thereof, it will be apparent to one skilled in the art that various changes and modifications can be made therein without departing from the spirit and scope thereof.

Other embodiments of the invention are found within the following claims.

We claim:

1. A sunscreen composition for application to human skin, said composition comprising
   a plurality of zinc oxide particles, each said particle having a substantially rod shape comprising a substantially spherical cross-section, smooth and rounded ends, and an aspect ratio of at least two, wherein said plurality of particles does not clump upon spreading on human skin; and
   an emollient for spreading on human skin,
   said plurality of particles being dispersed within said emollient in an amount effective to shield substantially all of said skin over which said composition is applied from hazardous effects of ultraviolet radiation.

2. The composition of claim 1 wherein said particles have a length of between 3 and 10,500 nanometers, inclusive, and a diameter of between 1 and 3,500 nanometers, inclusive.

3. The composition of claim 2, said particles having a length of less than 300 nm and a diameter of less than 100 nm.

4. The composition of claim 3, said particles having a length of less than 200 nm and a diameter of less than 65 nm.

5. The composition of claim 2, said particles having a length longer than 300 nm and a diameter greater than 100 nm.

6. The composition of claim 5, said particles having a length longer than 450 nm, and a diameter greater than 150 nm.

7. The composition of claim 2 wherein said zinc oxide particles comprise 0.1–50% of said composition by weight.

8. The sunscreen composition of claim 1 wherein said composition includes a sun protection factor of at least 2.

9. The suncreen composition of claim 8 wherein said sun protection factor is at least 15.

10. The sunscreen composition of claim 9 wherein said sun protection factor is at least 25.

11. The sunscreen composition of claim 1, each said substantially rod-shaped particle comprising the shape of a green bean.

12. A method of protecting human skin from hazardous effects of ultra-violet radiation, the method comprising
   applying to human skin an amount of a spreadable sunscreen composition effective to shield said skin over which said composition is applied from the hazardous effects of UV radiation, said composition comprising a plurality of zinc oxide particles, each said particle having a substantially rod shape comprising a substantially spherical cross-section, smooth and rounded ends, and an aspect ratio of at least two, wherein said plurality of particles does not clump upon spreading on human skin; and an emollient for spreading on human skin, said plurality of particles being dispersed within said emollient in an amount effective to shield substantially all of said skin over which said composition is applied from hazardous effects of ultraviolet radiation.

13. The method of claim 12, each said substantially rod-shaped particle comprising the shape of a green bean.

* * * * *